United States Patent
Soto Pérez et al.

(10) Patent No.: US 11,917,966 B2
(45) Date of Patent: Mar. 5, 2024

(54) SOY PLANTS COMPRISING THE TRANSGENIC EVENT CIGBDT-DEF1 OR CIGBIS-DEF5

(71) Applicant: CENTRO DE INGENIERÍA GENÉTICA Y BIOTECNOLOGÍA, Havana (CU)

(72) Inventors: Natacha Soto Pérez, Havana (CU); Gil Alberto Enriquez Obregon, Havana (CU); Celia Delgado Abad, Guantánamo (CU); Yamilka Rosabal Ayan, Havana (CU); Roxana Portieles Alvarez, Havana (CU); Sonia Gonzalez Blanco, Havana (CU); Maria Elena Ochagavia Roque, Havana (CU); Aneisi Reyes Migoyo, Havana (CU); Aleines Ferreira Fabré, Havana (CU); Merardo Pujol Ferrer, Havana (CU); Abel Hernández Velázquez, Havana (CU)

(73) Assignee: CENTRO DE INGENIERÍA GENÉTICA Y BIOTECNOLOGÍA, Havana (CU)

( * ) Notice: Subject to any disclaimer, the term of this patent is extended or adjusted under 35 U.S.C. 154(b) by 860 days.

(21) Appl. No.: 16/498,475

(22) PCT Filed: Mar. 29, 2018

(86) PCT No.: PCT/CU2018/050002
§ 371 (c)(1),
(2) Date: Sep. 27, 2019

(87) PCT Pub. No.: WO2018/177446
PCT Pub. Date: Oct. 4, 2018

(65) Prior Publication Data
US 2023/0135233 A1 May 4, 2023

(30) Foreign Application Priority Data
Mar. 31, 2017 (CU) .................. 2017-0042

(51) Int. Cl.
*A01H 5/10* (2018.01)
*A01H 6/54* (2018.01)
*C12N 15/82* (2006.01)
*C12Q 1/6895* (2018.01)

(52) U.S. Cl.
CPC ............ *A01H 6/542* (2018.05); *A01H 5/10* (2013.01); *C12N 15/8275* (2013.01); *C12N 15/8282* (2013.01); *C12Q 1/6895* (2013.01)

(58) Field of Classification Search
None
See application file for complete search history.

(56) References Cited

U.S. PATENT DOCUMENTS

2014/0007267 A1* 1/2014 Cole .................. A01H 1/02
435/6.12
2016/0138102 A1 5/2016 Kim et al.

FOREIGN PATENT DOCUMENTS

WO 2012051199 A2 4/2012

OTHER PUBLICATIONS

Portieles, R., et al., "NmDef02, A Novel Antimicrobial Gene Isolated from Nicotiana Megalosiphon Confers High-Level Pathogen Resistance Under Greenhouse and Field Conditions", Plant Biotechnology Journal 8, No. 6, pp. 678-690, 2010.
European Nucleotide Archive Search, Sequence AB209952.1, "Glycine Max Transgenic cp4epsps Gene for 5-enol-pyruvylshikimate-3-phospate synthase class 2 precursor, complete cds", https://www.ebi.ac.uk/ena/data/view/AB209952, accessed Oct. 4, 2019.
De Beer, A., et al., "Four Plant Defensins From an Indigenous South African Brassicaceae Species Display Divergent Activities Against Two Test Pathogens Despite High Sequence Similarity in the Encoding Genes." BMC Research Notes, 4:459, 2011, http://www.biomedcentral.com/1756-0500/4/459.
Pierozzi, P., et al., "New Soybean (*Glycine max* Fabales, Fabaceae) Sources of Qualitative Genetic Resistance to Asian Soybean Rust Caused by Phakopsora Pachyrhizi (*Uredinales*, Phakopsoraceae)", Genetics and Molecular Biology, vol. 31, No. 2, pp. 505-511, 2008.
Carmona, M., et al., "Uso de Mezclas de Azoxistrobina y Triazoles Para Controlar Enfermedades de Fin de Ciclo de la Soja", Summa Phytopathologica vol. 37, No. 2, pp. 134-139, 2011 (English Abstract only).
Funke, T., et al., "Molecular Basis for the Herbicide Resistance of Roundup Ready Crops", Proceedings of the National Academy of Sciences, vol. 103, No. 35, pp. 13010-13015, Aug. 29, 2006.
Kaur, J., et al., "Can Plant Defensins be Used to Engineer Durable Commercially Useful Fungal Resistance in Crop Plants?" Fungal Biology Reviews, vol. 25, No. 3, pp. 128-135, 2011.
Ntui, V., et al., "Stable Integration and Expression of Wasabi Defensin Gene in 'Egusi' Melon (*Colocynthis citrullus* L.) Confers Resistance to Fusarium Wilt and Alternaria Leaf Spot", Plant Cell Reports, vol. 29, No. 9, pp. 943-954, 2010.
Pandey, A., et al., "Functional Analysis of the Asian Soybean Rust Resistance Pathway Mediated by Rpp2", Molecular Plant-Microbe Interactions, vol. 24, No. 2, pp. 194-206, 2011.

(Continued)

*Primary Examiner* — Medina A Ibrahim
(74) *Attorney, Agent, or Firm* — Hoffmann & Baron, LLP

(57) ABSTRACT

The invention discloses a soybean plant, or a part of said plant comprising the transgenic event CIGBDt-Def1 or the transgenic event CIGBIs-Def5, as well as a method for the detection of those events in soybean samples. It also provides a seed from a soybean plant comprising said transgenic events, and products obtained from a plant, or from soybean seeds, comprising one of said events. In addition, the invention is related to a method for the production of soybean plants resistant to glyphosate, and to diseases caused by fungi or oomycetes, comprising the introduction of one of the mentioned transgenic events in the genome of said plants. The increase in the yield of a soybean crop in the field can be achieved with the transgenic events of the invention.

13 Claims, 7 Drawing Sheets

Specification includes a Sequence Listing.

(56) References Cited

OTHER PUBLICATIONS

Pérez-Vincente, L., et al., "First Report of Asian Rust of Soybean Caused by Phakopsora Pachyrhizi in Cuba", Plant Pathology, vol. 59, No. 4, p. 803, 2010.
Soto, N., et al., "Efficient Particle Bombardment-Mediated Transformation of Cuban Soybean (INCASoy-36) Using Glyphosate as a Selective Agent", Plant Cell, Tissue and Organ Culture (PCTOC), vol. 128, No. 1, pp. 187-196, 2017.
Torres, A., et al., "Bioassay for Detection of Transgenic Soybean Seeds Tolerant to Glyphosate", Pesquisa Agropecuária Brasileira, vol. 38, No. 9, pp. 1053-1057, 2003.
Zhu, S., et al., "Phylogenetic Distribution, Functional Epitopes and Evolution of the CSαβ Superfamily", Cellular and Molecular Life Sciences CMLS, vol. 62, pp. 2257-2269, 2005.
Sconyers, L. E., et al., "First Report of Phakopsora Pachyrhizi, The Causal Agent of Asian Soybean Rust, on Florida Beggarweed in the United States", Plant Disease, vol. 90, No. 7, p. 972, Jul. 2006.
Ribeiro, A. S., et al., "Genetic Control of Soybean (*Glycine max*) Yield in the Absence and Presence of the Asian Rust Fungus (*Phakopsora pachyrhizi*)," Genetics and Molecular Biology 31, No. 1:98-105, 2008.

\* cited by examiner

A

B

A

B

SEQUENCE LISTING

```
<160> NUMBER OF SEQ ID NOS: 8

<210> SEQ ID NO 1
<211> LENGTH: 22
<212> TYPE: DNA
<213> ORGANISM: Glycine max

<400> SEQUENCE: 1
aagcggcaag tcaatcgtgt cg                                        22

<210> SEQ ID NO 2
<211> LENGTH: 25
<212> TYPE: DNA
<213> ORGANISM: Glycine max

<400> SEQUENCE: 2
ctgaatccct acattgcgat tctcg                                     25

<210> SEQ ID NO 3
<211> LENGTH: 22
<212> TYPE: DNA
<213> ORGANISM: Glycine max

<400> SEQUENCE: 3
atgtgcaata attccttctt cg                                        22

<210> SEQ ID NO 4
<211> LENGTH: 20
```

```
<212> TYPE: DNA
<213> ORGANISM: Glycine max

<400> SEQUENCE: 4
cgaaacacga atcacgaagc                                           20

<210> SEQ ID NO 5
<211> LENGTH: 25
<212> TYPE: DNA
<213> ORGANISM: Agrobacterium tumefaciens

<400> SEQUENCE: 5
ggatttcagc atcagtggct acagc                                     25

<210> SEQ ID NO 6
<211> LENGTH: 23
<212> TYPE: DNA
<213> ORGANISM: Agrobacterium tumefaciens

<400> SEQUENCE: 6
gcgggttgat gacttcgatg tcg                                       23

<210> SEQ ID NO 7
<211> LENGTH: 24
<212> TYPE: DNA
<213> ORGANISM: Nicotiana megalosiphon

<400> SEQUENCE: 7
gctggcttat gcttcctctt cttg                                      24

<210> SEQ ID NO 8
<211> LENGTH: 22
<212> TYPE: DNA
<213> ORGANISM: Nicotiana megalosiphon

<400> SEQUENCE: 8
tcacagactt ggacgcagtt cg                                        22
```

SOY PLANTS COMPRISING THE TRANSGENIC EVENT CIGBDT-DEF1 OR CIGBIS-DEF5

CROSS-REFERENCE TO RELATED APPLICATIONS

This application is a U.S. National Phase of, and Applicant claims priority from, International Patent Application No. PCT/CU2018/050002, filed Mar. 29, 2018, which claims priority from CU 2017/0042, filed Mar. 31, 2017, each of which is incorporated herein by reference in its entirety.

FIELD OF THE INVENTION

The present invention is related to plant biotechnology, specifically to the protection of soybean against diseases caused by fungi and oomycetes in commercial genotypes of said crop. Particularly, the invention is related to two new transgenic events, resulting from the genetic transformation of two soybean genotypes. The events were designated as CIGBDt-Def1 and CIGBIs-Def5.

BACKGROUND OF THE INVENTION

Plants are constantly exposed to different pathogens present in nature. As a consequence, they have developed a complex defense system to be protected against the attack of said pathogens. These defense systems can be classified, according to the moment of their expression, in constitutive, if they are present during the whole life cycle of the plant; and induced, if their expression is evidenced in a larger proportion facing the presence of a pathogen. One of these mechanisms consists of plant defensins. These compounds are small cationic peptides having from 45 to 54 amino acid residues, with disulphide bridges in the cysteines contained within them (Zhu et al., Cell Mol. Life Sci. (2015) 62: 2257-2269). Plant defensins were firstly described in wheat and barley seeds, and their role in the defensive system of this type of organisms have been well characterized. They are distributed in correspondence with the role that they play in the biological system and the expression profile, according to the action mode of the peptide (Beer and Vivier, BMC Res. Notes (2011) 4:459).

Soybean plants are affected by diverse diseases that impact negatively in yields and in the quality of the seeds, causing total losses of the production. The most important diseases are those caused by fungi, due to the magnitude of the damages they cause. For conventional programs for the improvement of the soybean crop, it has been extremely difficult to obtain commercial genotypes that show resistance to the main fungal infections that affect this crop.

Up to now, the application of chemical fungicides is the most effective treatment for the control of the fungi pathogens of soybean. However, their application has been reduced, due to the high amount of active ingredients in these products that produced pathogen resistance against some fungicides. Also, their use increases the production costs, so the development of resistant varieties is considered as the more economic control strategy.

Within fungi that affect the soybean crop, the *Colletotrichum* genus has great importance, as it is the causal agent of anthracnose, a typical disease of tropical and subtropical countries that appears since the initial phases of the plant development. This disease causes great affectations to the quality of the grains, causing the death of seedlings, due to the absence of symptoms in the seeds when the infection is mild. In this way, the fungus may cause deterioration in the seeds and systemic infection in mature plants, and the damages become worse with the rains, the excessive density of the population, or when the crop is late, reducing the yields (Gally et al., Integrated management of plagues and Agroecology (2006) 78: 86-90). The "end-of-cycle" diseases of soybean are the most frequent, and they may cause damages of approximately 8% to 10% of the yield, with a maximum up to 30%. The symptoms vary according to the existing infection, and are shown in intermediate and advanced reproductive states. Those that stand out more are the decrease of the healthy leaf surface, the premature defoliation of plants, the premature maturity of the crop, and the decrease of seed quality. Among the diseases that form the so called "end-of-cycle-complex" there are the stem rust and the purple speck (caused by *Cercospora kikuchii*), frog eye spot (caused by *Cercospora sojina*), seed ringspot (caused by *Corynespora cassiicola*), seed brown spot (caused by *Septoria glycines*), stem rust and sheath spot (caused by *Phomopsis sojae*), mildew (caused by *Peronospora manshurica*), alternaria foliar spot (caused by *Alternaria* spp.), anthracnose (caused by *Colletotrichum truncatum*) and the Asian rust, among others (Carmona et al., Phytophatologica (2011) 37: 134-139).

*Phakopsora pachyrhizi* is the causal agent of Asian soybean rust (Torres et al., Pesq. Agropec. Bras (2012) 38:1053-1057). This disease is considered the most devastating that affects the crop, since it impacts in precocious defoliation and affectation of the main components of yield, and it causes losses of 10 to 90% of the production (Ribeiro et al., Genetics and Molecular Biology (2008) 31:98-105). It was detected in the American continent in 2001, and it has caused heavy losses to soybean production in South America. In Cuba, the presence of Asian rust was detected in 2010 (Perez et al., Plant Pathology (2011) 59:803) and it was disseminated through different soybean producer provinces.

Two rust types have been identified in soybean. Besides from Asian rust, the American rust of soybean, caused by *P. meibomiae*, has been reported. The structures useful to differentiate between both rust species are the telospores. However, these are difficult to find, due to the impossibility of in vitro culture of both pathogens. For a correct identification, molecular techniques as the polymerase chain reaction (PCR) with specific oligonucleotides for *P. pachyrhizi* can be used. The presence of Asian rust in the field can be determined by using immunochromatographic diagnostic strips, these are able to detect the presence of the pathogen in the initial states of the infection, and they are designed to be used in the leaf tissue.

Under good environmental conditions (6 hours of dew as minimum and temperatures between 18 and 25° C.), the infection by *P. pachyrhizi* progresses quickly, and it causes precocious defoliation. It results in a decrease in the number of sheaths, grains and their weight (Pandey et al. Molecular Plant-Microbe Interactions (2010) 24:194-206).

Several experiments indicate that the plant defensins are involved in protection of the host against pathogen attack. For example, the Hc-AFP1-4 defensins, isolated from the *Heliophila coronopifolia* species, showed in vitro inhibitory activity against *Botrytis cinerea* and *Fusarium solani*. The Rs-AFP1 and Rs-AFP2 defensins are strongly induced in radish leaves after the infection with *Alternaria brassicola*, showing "in vitro" antifungal activity.

Studies carried out by Portieles and collaborators demonstrated that the constitutive expression of the gene of nmdef02 defensin, isolated from *Nicotiana megalosiphon*, provides resistance to transgenic potato and tobacco plants, against *Phytophthora infestans*, *Alternaria solani* and *Fusarium oxysporum*, in field conditions. These authors also observed a strong in vitro antimicrobial activity of nmdef02 defensin against pathogens as *Phytophthora infestans*, *Phytophthora parasitica* var. *nicotianae*, *Alternaria solani*, *Fusarium oxysporum* var. *cubense*, *Verticillium dahliae* (Portieles, et al., Plant Biotechnology Journal (2010) 8:678-690). It confirms the important role of the defensins in protection against phytopathogens.

On the other hand, the production of transgenic lines of soybean resistant to herbicides is one of the biotechnology applications in modern agriculture. The expression in plants of an *Agrobacterium* gene linked to the metabolic route of shikimate confers resistance to the herbicide glyphosate (N-phosphonomethylglycine), at the field dose, in modified crops. Glyphosate interrupts the synthesis of the aromatic amino acids in plants, through the competitive inhibition of 5-enol-pyruvyl shikimate-phosphate synthetase enzyme (Funke, et al., PNAS (2006) 103 (35): 13010-5). The presence of the herbicide in the meristems of the plants inhibits growth, and it causes their death. However, the soybean transgenic plants that contain the cp4epsps gene (whose sequence appears in the GenBank database of NCBI, with access No. AB209952.1) continue the synthesis of aromatic amino acids in presence of the herbicide.

The genetic transformation of soybean genotypes of commercial interest is convenient, to obtain transgenic materials with protection against of a variety of fungi and oomycetes of incidence in the soybean crop, and where the use of the glyphosate herbicide, to control the weeds that affect said crop, can be employed.

INCORPORATION OF SEQUENCE LISTING

Figure 1:
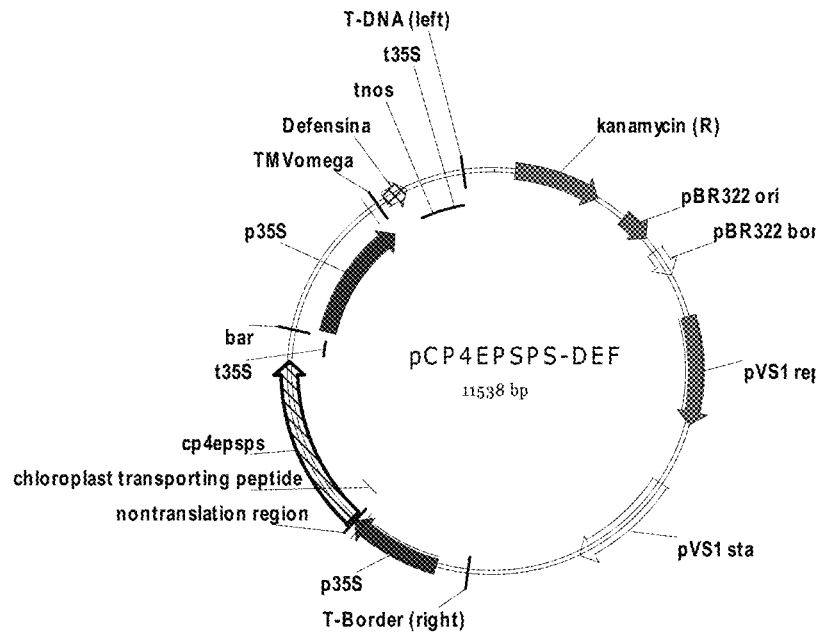
FIG. 1. Map of plasmid pCP4EPSPS-DEF used for the transformation of meristematic soybean tissues by *Agrobacterium* and gene gun.

Incorporated herein by reference in its entirety is the Sequence Listing for the application. The Sequence Listing is disclosed on a computer-readable ASCII text file entitled "Soybean Plants Comprising the Transgenic Event CIGBDT-DEF1 or CIGBIS-DEF5", created on Sep. 27, 2019. The Sequence Listing .txt file is 33.2 KB (34,030 bytes) in size.

DESCRIPTION OF THE INVENTION

The present invention solves the problem mentioned above, providing a soybean plant, or a part of said plant, comprising the transgenic event CIGBDt-Def1 or the transgenic event CIGBIs-Def5. Soybean seeds representatives of both events were deposited at the National Collection of Industrial, Food and Marine Bacteria (NCIMB), of the United Kingdom, institution acting as an International Deposit Authority. The representative seeds of the CIGBDt-Def1 event were deposited under access number NCIMB 42724, and the seeds representative of the CIGBIs-Def5 event were deposited under access number NCIMB 42725. These transgenic events were obtained by genetic engineering and, in a singular manner; they confer autofungicide activity to the plant containing them. In this way, the transgenic plant is able to evade the negative effect caused by fungal and oomycete pathogens in the soybean crop. The two transgenic events of the invention express the nmdef02 defensin gene, and the cp4epsps gene responsible for the resistance to the glyphosate herbicide, and they were generated by the *Agrobacterium* method or by gene gun.

In the present invention, "soybean plant" refers to all the plants of the *Glycine max* species, and it includes all the varieties of soybean with commercial interest, also containing all the parts of the plant.

In the invention the soybean event named CIGBDt-Def1 is also referred as CIGB-DtDEF1, DTDef1, DtDEF1 and DtDef1. On the other hand, the soybean event named CIGBIs-Def5 is also referred as CIGB-IsDEF5, IsDEF5 and IsDef5. Besides the characteristic sequences of each one of these events, the soybean plants of the invention may contain additional sequences of deoxyribonucleic acid (DNA), flanking said sequences. Other transgenic events that were also obtained, and are mentioned in the examples of the invention, were named using the combination of Dt (or DT) and Is (or IS) and the number of the corresponding event, for example, Dt12, Is20, etc.

The events CIGBDt-Def1 and CIGBIs-Def5 were obtained from two conventional soybean varieties: Dt84 and Incasoy36 (Is36). The expression of the defensin coded by the nmdef02 gene is important for the protection against phytopathogenic fungi associated to the crop, which limit the production levels as well as the quality of the grain. The plants comprising these transgenic events tolerate up to five times the effective dose in field conditions of the non-selective herbicide glyphosate, allowing the use of this herbicide for the control of weeds under production conditions.

In an embodiment, the invention reveals a soybean plant that is the progeny of any generation of a soybean plant comprising the event CIGBDt-Def1 or the CIGBIs-Def5. In another embodiment, the invention provides a soybean plant that is the result of the crossing of a soybean plant comprising the transgenic event CIGBDt-Def1 or the CIGBIs-Def5 with a non-transgenic soybean plant.

The term "transgenic" includes any line, plant, cell or event that has been modified by the presence of a heterologous nucleic acid that includes those originally modified transgenics, as well as those created by sexual crossings or asexual propagation of the initially regenerated event.

In the invention, the term "progeny" refers to the plants produced by means of a sexual cross (for example, backcross, self-cross or intercross) between a plant comprising the events CIGBDt-Def1 and CIGBIs-Def5 and another commercial soybean genotype.

In the way that is used here, the term "part of the plant" includes plant cells, plant organs, vegetal protoplasts, vegetal cell tissue cultures, from which the plants can be regenerated, plant callus, seedlings and intact vegetal cells in the plants. The term "part of the plant" also includes embryos, pollen, ova, seeds, sheaths of seeds, leaves, flowers, branches, stems, roots, apexes of the roots, anthers, cotyledons, hypocotyls, and similar ones. The term "grains", means the mature seed produced by commercial farmers with goals different from growth or reproduction of the species.

In an embodiment, the invention is related to a part of the plant comprising the event CIGBDt-Def1 or CIGBIs-Def5, where the part can be a root, bud, leaf, pollen, ovum, flower or cell. The invention also provides a seed of a soybean plant comprising the event CIGBDt-Def1 or CIGBIs-Def5.

In this invention the term "transgenic line" refers to a plant whose genome has been modified, by means of genetic engineering, to introduce one or several new genes from a non-related plant, or from a different species; or to modify the function of an own gene. As a consequence of the insertion or modification of the gene, the transgenic line shows a new characteristic, regularly transmitted to the descendants, from a certain clonal generation.

In the invention, the soybean plants can acquire a new phenotype, additional to the one that they already have with the events of the invention, and for that purpose the transformation of vegetal material or explants derived from the plants that comprise the events can be used. Said characteristics, additional to the referred events, can be acquired by anyone of the available methods of genetic transformation. The term "transformation" refers to the transfer of a fragment of nucleic acid in the genome of a guest organism, giving place to a genetically stable inheritance.

The plants comprising the events CIGBDt-Def1 or CIGBIs-Def5 can be used as a source of vegetal material in transformation methods, to introduce the molecules of heterologous nucleic acid to new soybean events. Transformation vectors to introduce other genes of interest could be prepared, and as a consequence other lines with different characters introduced in the same plant can be achieved.

A "transgenic event" is produced by the transformation of vegetal cells with a genetic construction that contains the heterologous DNA, including an expression cassette of nucleic acid comprising a transgene of interest, the regeneration of a population of plants that results from the insertion of the transgene in the plant genome, and the selection of a particular regenerated plant. The event is characterized by the location of the insertion in a particular genome and phenotypically by the expression of the transgene or the transgenes. At the genetic level, an event is a DNA segment that is part of the genetic composition of a plant. In the present case, the transgenic events contain two transgenes.

In other aspect, the invention provides a soybean product that is produced from a plant or a soybean seed comprising the event CIGBDt-Def1 or CIGBIs-Def5. In an embodiment of the invention, the product consists of flour, flakes, oil or a product for human or animal feeding.

Another aspect of the invention is a method for the production of soybean plant resistant to the herbicide glyphosate and to diseases caused by fungi or oomycetes wherein the event CIGBDt-Def1 or CIGBIs-Def5 is introduced in the genome of said plant. In an embodiment of the invention, the soybean disease is the Asian rust, caused by *P. pachyrhizi*. In the invention, plants resistant to the Asian rust are those plants of a line where the presence of symptoms of this disease does not exceed 50% of the plants under natural infection conditions.

In an embodiment of the invention, said method comprises the cross of a soybean plant comprising the event CIGBDt-Def1 or CIGBIs-Def5 with another soybean plant, and the selection of the progeny comprising one of these events.

Is also an object of this invention, a kit of reagents for the detection of nucleic acid corresponding to the event CIGBDt-Def1 or CIGBIs-Def5, in a sample of soybean genomic nucleic acid, wherein said kit comprises at least a pair of oligonucleotides for the amplification of nucleic acid fragments corresponding to the regions of union between the nucleic acid of a soybean plant and the nucleic acid corresponding to the event CIGBDt-Def1 or CIGBIs-Def5.

The design and usage of a useful oligonucleotide or primer pair is possible, including a primer that overlaps the point of union between the DNA of the insert and the 5' extreme of the flanking DNA; or the DNA of the insert and the 3' extreme of the flanking DNA. The methods to design, obtain and use DNA probes or primers in the present invention are known in molecular biology. The PCR primer pairs can be derived from a known sequence, for example, by using computer programs developed with this purpose, such as the PCR primer analysis tool in its version 11 of the Vector NTI (Thermo Fisher Scientific).

In other aspect, the invention provides a method for the diagnosis of the event CIGBDt-Def1 or CIGBIs-Def5 in a soybean sample comprising analyzing said sample to detect the presence of nucleic acid or protein corresponding to the event CIGBDt-Def1 or CIGBIs-Def5.

In this document, a "sample" includes any fraction that contains nucleic acids or polypeptides and is obtained from a plant, vegetal material or products, such as feed for animal consumption or fresh or processed products derived from the vegetal material.

According to the method for the diagnosis of the event CIGBDt-Def1 or CIGBIs-Def5 that is chosen, it is possible, for example, to analyze a sample obtained from a soybean plant, including the progeny, in addition to the by-products of said plants. Such methods find their application in the identification or detection of regions or molecules of nucleic acid of the referred events, in any biological material. Such methods include, for example, the methods to confirm the purity, and methods for the screening of seeds, in a batch of seeds that comprise the nucleic acid molecules characteristic of the transgenic event CIGBIs-Def5 or CIGBDt-Def1. In Example 3, a method for the identification of nucleic acids from the events of the invention in a biological sample is shown. This method comprises the preparation of a mixture of a biological sample and a pair of primers complementary to the nucleic acid, able to amplify specific regions in the nucleic acid molecule of the events CIGBIs-Def5 and CIGBDt-Def1.

Within the diagnosis or detection methods of the events of the invention is any method to amplify the molecule of nucleic acid of the event CIGBIs-Def5 or CIGBDt-Def1 by PCR. In addition, said events can be detected or identified by the detection of the polypeptide or a peptide of the defensin, expressed in the soybean plants. Any method can be used in the detection of the polypeptide or peptide. For example, antibodies specific to the defensin can be used and any known immunochemical method, such as ELISA, Immunoblot, or Dot Blot can be employed.

In a particular embodiment of the invention, the diagnosis of the event CIGBDt-Def1 or CIGBIs-Def5, in a soybean sample, is characterized by the use of a kit of reagents that comprise at least a pair of oligonucleotides for the amplification of the nucleic acid fragments corresponding to the union regions between the nucleic acid of a soybean plant and the nucleic acid corresponding to the event CIGBDt-Def1 or CIGBIs-Def5.

The invention also provides a method to increase the yield of a soybean crop in field comprising to sow seeds from a soybean plant comprising the event CIGBDt-Def1 or CIGBIs-Def5, to establish the soybean crop in the field, and to treat the field with an effective quantity of the herbicide glyphosate to control the weeds. In an embodiment of the invention in said method the field is treated between the phases V1 and R4 of the crop. The methods of establishment of the soybean crop and the herbicide application are very well-known by those skilled in this technical field.

The soybean plants that comprise the event CIGBDt-Def1 or CIGBIs-Def5 can be used in an improvement program, using methods of cross or hybridization, to reproduce these events in soybean plants of other genotypes. Such improvement methods can be employed to produce soybean plants, for example, for their use in the commercial production in different geographical regions, or to produce additional populations for soybean reproduction.

Moreover, the plants that bear the events of the invention can be used in reproduction programs, using improvement methods, to produce soybean plants with additional characteristics of interest, that could be combined with the tolerance to the herbicide glyphosate and the resistance to fungi (also referred as "piled traits"). For example, an additional characteristic could be the resistance to additional herbicides, such as glufosinate, and the combination with other agronomical important traits, including the resistance to other diseases and pathogens (for example, Bt genes), as well as the improvement of traits referred to the quantity and quality of oils and proteins present in the soybean grain.

These combinations of desired characteristics (piled) can be created by any method, including, but not limited to, the improvement of the plants by any known methodology, or by genetic transformation. If the sequences are piled, by means of the genetic transformation of the plants, the nucleic acid sequences typical of the event CIGBDt-Def1 or CIGBIs-Def5 can be combined in any moment, and in any order. The traits can be introduced simultaneously, by means of co-transformation with the molecules of nucleic acid of interest, provided by any combination of transformation cassettes. For example, if two additional sequences are introduced, the two sequences can be contained in separate transformation cassettes (trans) or in the same transformation cassette (cis). The expression of the sequences can be regulated by the same promoter or by different promoters.

In certain cases, it can be desirable to introduce a transformation cassette that suppresses the expression of a molecule of nucleic acid of interest. This can be adjusted with any combination of other suppression cassettes or overexpression cassettes to generate the expected combination of characteristics in the plant. It is also recognized that the molecules of nucleic acid can be piled in a wanted genomic localization, by using a system of site-specific recombination.

EXAMPLES

Example 1. Regeneration of Plants from Embryogenic Tips of the Dt84 and Is36 Genotypes The embryonic axes were obtained from surface sterilized seeds of the Dt84 and Is36 varieties, coming from the National Institute of Agricultural Sciences. The seeds were decontaminated by means of incubation for one minute in 70% ethanol, and then in a solution of 10% hydrogen peroxide (v/v), during 7 hours, and after successive rinses with sterile distilled water. The decontaminated seeds were left at rest, submerged in sterile distilled water, during 28 h, to room temperature and in the darkness. Then it was proceeded to eliminate the bark of the seeds on a Petri dish, and to separate the cotyledons to extract the embryo that was used as explant in the transformation and soybean regeneration experiments. Later on, it was proceeded to eliminate the primary leaves, with the help of a stereoscope, to leave exposed the apical meristem, and 15 embryos were placed with the apical meristem region up, in dishes that contained MS medium (Murshige and Skoog Plant Physiol (1962) 15:473-479).

Regeneration of shoots from the meristematic apical area of the explants was achieved, after 10-15 days, in the three tested combinations of crop media. In variant A with benzyladenine (BAP) at 0.2 mg/L, and 0.2 mg of indolebutyric acid (IBA)/L, a high regeneration frequency was obtained (83%), a relatively short time (20 days), and with a regeneration efficiency of 1.6 shoots per explant. The defined shoots began to take root in the regeneration medium, and the apparition of white and thin roots was observed, after 15 days. The base of buds that had not taken root at 15 days was cut, and they were passed to fresh medium, where 90% developed roots satisfactorily.

Combination BAP/IBA in the culture medium favored regeneration of buds, starting from the apical area of the meristematic axis, but it caused an abundant formation of callus in the radicle area. For this reason, the response of the explants was evaluated in a regeneration medium without auxin (variant B). The results obtained in the regeneration of buds were similar in variants A and B, nevertheless it was achieved a larger regeneration frequency and a larger number of buds in the variant without IBA.

On the other hand, regeneration of buds in a medium without hormones (variant C) was superior to the one in the variants with hormones. The induction of buds in 5 mg/L of BAP, for 48 h, was enough to achieve an efficient regeneration, and a larger number of buds per explant in the MSB5 medium (MS Medium supplemented with B5 vitamins). Pre-treatment with 5 mg of BAP/L favored the formation of multiple buds, after 25 days in MSB5 medium, which began being defined when they passed to fresh medium. These buds regenerated normal buds, leaves and small buds that did not grow.

Later on, it was repeated the regeneration experiment with pre-treatment in 5 mg of BAP/L, in the Is36 and Dt84 varieties. The results were superior after having optimized this regeneration system. All explants regenerated buds, and it was achieved an efficiency of regeneration of 2.6 and 3.7 shoots by explant, respectively, as it is shown in Table 1. The data are the average of two experiments.

TABLE 1

Regeneration of buds from the embryonic axis of mature seeds, after an induction period of 48 h in 5 mg of BAP/L.

| Genotype | No. of explants | Total explants with shoots | Total shoots | Regeneration percentage (%) | Shoots/explants |
|---|---|---|---|---|---|
| Is36 | 29 | 29 | 74 | 100 | 2.6 |
| Dt84 | 28 | 28 | 103 | 100 | 3.7 |

Example 2. Development of Transgenic Soybean Lines

With the objective of establishing a transformation protocol in the meristematic tissues of soybean seeds, 100 explants were bombarded with the pCambia 2301 (CAMBIA, Canberra, Australia). The histochemical test of β-glucuronidase (GU) confirmed the presence of enzymatic activity in 56 of the 100 explants, after 48 h, in a shoot induction medium with 5 mg of BAP/L. The transitory expression of GUS was evident in regions that are characterized by a strong division capacity, as the apical area of the embryonic axes and the tip of the radicle.

To determine the optimum minimum lethal concentration to select the transformed buds, firstly the response of the soybean embryonic axes was evaluated facing different glyphosate concentrations. The explants in MSB5 medium without selection, used as control of the regeneration, showed 100% of shoots regeneration. In this experiment, the sensibility to glyphosate became evident in the concentration of 15 mg/L, where only 16% of the embryonic axes showed the development of buds and leaves, after 35 days. Similar results were observed in 20 mg/L of glyphosate, with 6% regeneration after 50 days. All the explants maintained their green color, in spite of showing their sensibility to the herbicide in the apical area of the embryonic axes. Only a total inhibition of morphogenesis was achieved after 60 days in 25 mg/L of glyphosate. In this concentration, some explants exhibited necrosis in the apical region. Finally, it was determined that 25 mg/L of glyphosate in the MSB5 medium was enough to inhibit the normal differentiation of the untransformed shoots. For that reason, this concentration was used in the experiments of genetic transformation with the cp4epsps gene, for the selection of buds tolerant to glyphosate.

Once established the conditions for the selection, the apical region of the embryonic axes was bombarded with plasmid pCP4EPSPS (Soto et al., Plant Cell Tissue & Organ Culture (2017) 128:187-196), and transgenic soybean plants were obtained that carry the cp4epsps gene. Induction of shoots happened after 48 h, in 5 mg/L of BAP, and the explants were sub-cultured to the MSB5 medium with 25 mg/L of glyphosate. The negative control in MSB5 with selection did not show any morphogenesis, and the explants maintained their green coloration. In the positive control the development of well-defined buds was observed (2 cm) after 10 days in MSB5 without selection.

In these experiments, the meristematic tissues of the embryonic axis were bombarded solely once, which was enough to reach the shoots tolerant to the herbicide without damages in the explants. The data showed that 32 of the 705 bombarded explants (4.5%) developed shoots in presence of the herbicide, that represents an average of transformation efficiency that varies from 5.0 to 8.5% (defined as the total of plants tolerant to glyphosate divided by the total number of bombarded explants). After 15 to 20 days in selection, the first buds appeared in the explants, by means of direct organogenesis. All the regenerated shoots that achieved a size from 3 to 4 cm were transferred to medium rooting without selection. After 15 days, 46 plants formed roots, and they showed a similar phenotype to the one of non-transgenic plants. The plants developed a main root, with secondary roots with radical hairs that favored the growth and formation of new leaves at a short time (10-15 days).
Genetic Transformation with Plasmid pCP4EPSPS-DEF As said previously, for the genetic transformation of soybean it is settled down that 25 mg/L of glyphosate is the lethal minimum concentration of the herbicide for the in vitro selection of the tolerant shoots. The apical region of the embryonic axes was bombarded with plasmid pCP4EPSPS-DEF, represented in FIG. 1. Here below the genetic elements incorporated in this plasmid are described: T-Border (right): Right border; P35S: Promoter corresponding to the virus of the mosaic of the cauliflower (CaMV 35S); cp4epsps: Resistance gene to glyphosate herbicide; t35S: Terminator corresponding to CaMV 35S; Defensin: Defensin gene nmdef02 for resistance to fungi; TMVomega: Leader sequence of tobacco mosaic virus (TMV); tnos: Terminator of nopaline synthase; T-DNA (left): Left border; Kanamycin (R): npt II gene for resistance to kanamycin; pBR322 ori: Origin of replication of plasmid pMB1; pVS1: Origin of replication derived from *Pseudomonas aeruginosa*.

The bombarded explants, after 48 h in induction with BAP, grew quickly. All the embryonic axes changed from white color to green dark, after 7 days in the MSB5 medium with glyphosate selection, and under a of light and darkness photoperiod. In the positive control, the development of defined buds was observed (2 cm) after 10 days, in MSB5 medium without a selection agent, for Dt84 and Is36 genotypes. On the other hand, the explants cultured in MSB5 medium with 25 mg/L of glyphosate that were used as negative control, did not show regeneration of the shoots, although they maintained the green coloration.

In these experiments, there were bombarded a total of 177 explants of variety Dt84, and 219 explants of variety Is36, which showed a frequency of regeneration of 10.7% and 6.8%, respectively; under a pressure of selection of 25 mg/L of herbicide. The regeneration of shoots began to be observed after 15 days in the MSB5 medium with selection, being achieved an efficiency of transformation of 13.5% (Dt84) and 10.5% (Is36). When the shoots regenerated in glyphosate reached a size of 3-4 cm, they passed to take root in the rooting medium, without selection. After 10 days, the plants took root and they had a normal development, similar to the untransformed control.

The embryonic axes of cultivating Is36 were used for the transformation via *Agrobacterium tumefaciens*, for which the LBA4404 strain was transformed with pCP4EPSPS-DEF plasmid (FIG. 1). The procedure consisted on the crop from the bacteria to an optic density to 620 nm of 0.8; and later on the infection of explants, during 30 minutes, in presence of 200 µM of acetosyringone. Explants were co-cultured under conditions of darkness, during 48 hours, and they were transferred to MSB5 medium with 25 mg/L of glyphosate. The defined shoots that emerge from the infested explants were cultured in a medium without selection, to achieve their rooting. The rooting shoots were adapted under natural conditions, for their molecular and biological characterization.

Figure 2:
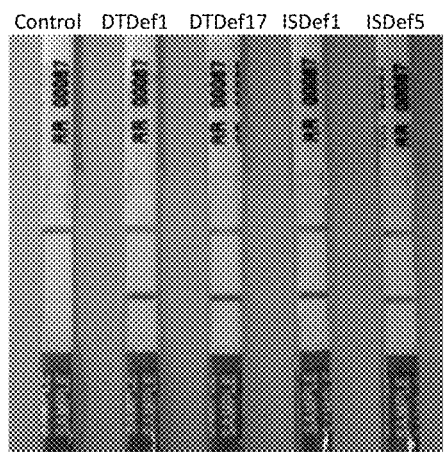
FIG. 2. Immunodetection of pCP4EPSPS Roundup Ready Protein®. The four strips to the right (with two signals) correspond to transgenic soybean lines. The strip to the left (with a single signal) corresponds to the untransformed soybean control. The upper line works as positivity control of the strip and the lower line indicates the reactivity with an antiCP4EPSPS antibody.

All the transformed lines (TO) resistant to the herbicide were positive in the qualitative test of expression of the CP4EPSPS protein, carried out with the Roundup Ready® immunodetection kit, as it is shown in the strips corresponding to four transformed lines tolerant to herbicide glyphosate (FIG. 2).

Figure 3:
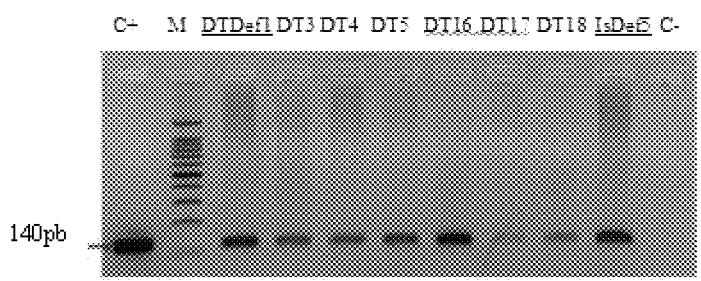
FIG. 3. PCR products from genomic DNA of soybean plants transformed with plasmid pCP4EPSPS-DEF and the non-transgenic control. Amplification of a sequence of 140 bp corresponding to the nmdef02 gene. C+: plasmid pCP4EPSPS-DEF. M: Molecular weight marker (Promega). Lanes DTDef1, DT3, DT4, DT5, DT16, DT17, DT18 and IsDef5: transgenic soybean lines. C-: untransformed plants.

Example 3. Molecular Characterization of Transgenic Soybean Lines Transformed with Plasmid pCP4EPSPS-DEF To carry out the characterization, genomic DNA was isolated from young leaves of transgenic plants (T2 generation) and of the untransformed control. All the transgenic lines tolerant to the herbicide glyphosate (and positive for the immunodetection kit of CP4EPSPS protein) were analyzed by PCR, to confirm the presence of the nmdef02 gene. In this analysis a signal of 140 bp was obtained that corresponds with the expected size to confirm the presence of this gene, so much in the seven lines derived from genotype DT, as in those derived from genotype Is36, where the line selected was IsDef5. The results of this analysis are shown in FIG. 3. In the untransformed plants, used as negative control, a reaction of amplification of the defensin gene was not detected.

Figure 4:
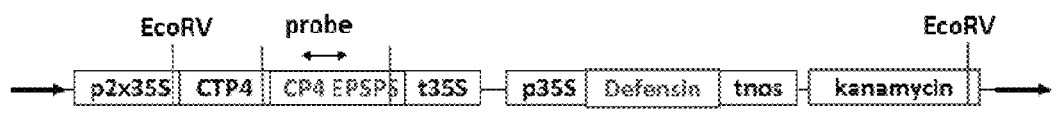
FIG. 4. Representation of pCP4EPSPS-DEF plasmid fragment that contains the two restriction sites of the EcoRV enzyme (5.3 Kb) and the fragment of the cp4epsps gene used as a probe (886 bp).

To evaluate the stability of the genes in an advanced generation (T3), the genomic DNA of the transgenic plants of that generation, and of the untransformed control, it was digested with the EcoRV enzyme. This enzyme has two restriction sites in plasmid pCP4EPSPS-DEF, just as it is shown in FIG. 4. The digested genomic DNA was analyzed, by means of Southern blot, to determine the integration of the plasmid in the transgenic soybean events.

Figure 5:
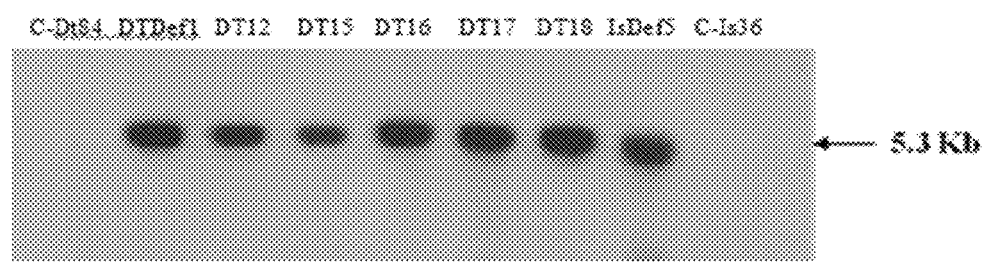
FIG. 5. Southern blot for the detection of the integration of the cp4epsps and nmdef02 genes in soybean events (T3). DTDef1, Dt12, Dt15, Dt16, Dt17, Dt18 and IsDef-5: transgenic soybean lines. C-Is36 and C-Dt84: untransformed plants.

Southern blot results are shown in FIG. 5, where the signals corresponding to the region of the plasmid between the two sites that are recognized by the EcoRV enzyme are visualized. These signals demonstrate the integration of the segment of the plasmid that contains cp4epsps and nmdef02 genes in the genome of the DtDef1, Dt12, Dt15, Dt16, Dt17, Dt18 and the IsDef5 plants, which present a hybridization signal with a size of 5.3 Kb. The DNA of the plants of untransformed soybean, used as negative control, did not show any hybridization signal.

Figure 6:
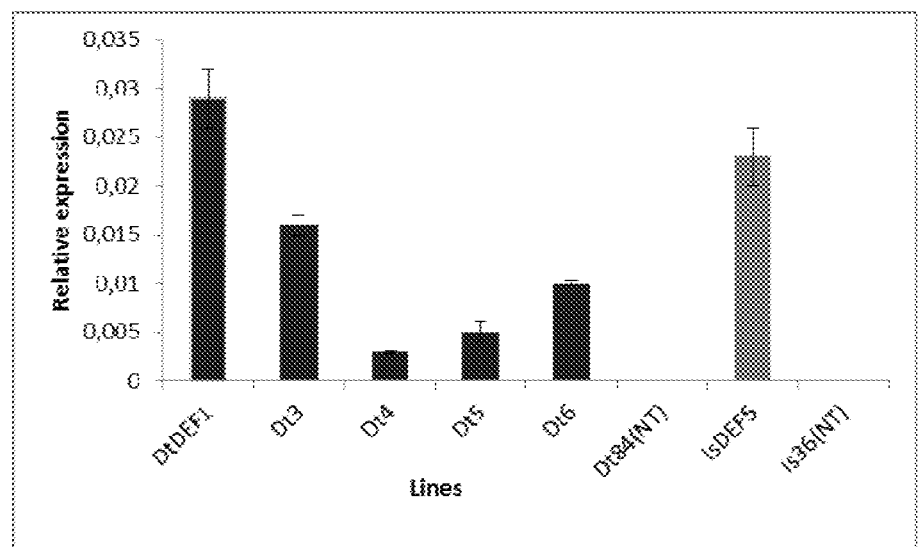
FIG. 6. Relative expression of the nmdef02 gene in transgenic soybean plants transformed with plasmid pCP4EPSPS-DEF. The Real-Time Quantitative Reverse Transcription PCR (qRT-PCR) was used to measure the levels of transcripts of the nmdef02 defensin gene, compared to the constitutive expression of endogenous actin of the untransformed control Dt84. Transgenic lines: DtDef1, Dt3, Dt4, Dt5, Dt6 and IsDef5. Untransformed controls: Dt84 (NT) and Is36 (NT).

The analysis of the relative expression of nmdef02 defensin gene was carried out in the transgenic lines (Dt-Def1; Dt3; Dt4; Dt5; Dt6 and IsDef5), of the T2 generation, by means of qRT-PCR, to select those of more expression for the field tests. The evaluated lines showed different levels of expression of the defensin gene as it is shown in FIG. 6. It was demonstrated that the levels of accumulation of the transcript of the nmdef02 gene were superior in the DtDef1 and IsDef5 lines, followed by Dt3 and Dt6, so they were chosen for the evaluation in field, in front of fungal pathogens. It was proven in this analysis that these lines were significantly different to the rest of the lines and to the non-transgenic control (p<0.0001).

Figure 7:
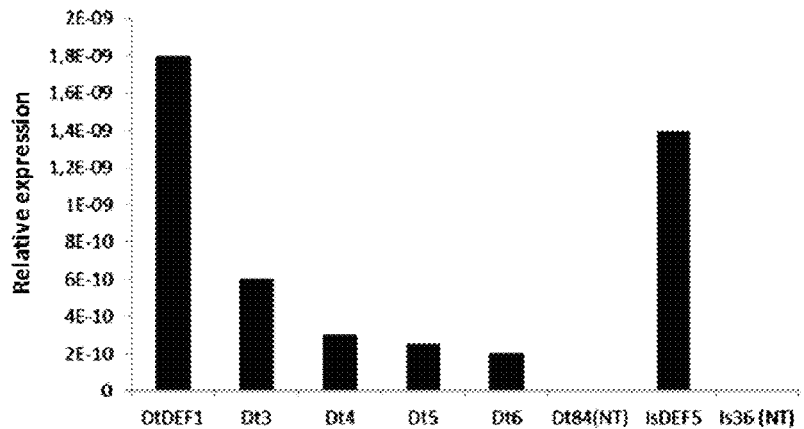
FIG. 7. Relative expression of the nmdef02 gene in transgenic soybean plants of the T3 generation. The bars represent the mean of the results obtained from three replicates for p<0.0001. The qRT-PCR was used to measure the levels of transcripts of the nmdef02 defensin gene, compared to the constitutive expression of endogenous actin in the untransformed control. Transgenic lines: DtDef1, Dt3, Dt4, Dt5, Dt6 and IsDef5. Untransformed controls: Dt84 (NT) and Is36 (NT).

The analysis by qRT-PCR was carried out again in the same lines, but in the T3 generation. The result showed that all the lines showed levels of nmdef02 expression different to their respective controls, as it is appreciated in FIG. 7, which coincides with that observed in the evaluation of the precedent generation. The DtDef1 and IsDef5 lines showed again the largest levels of relative expression, with a highly significant difference in relation to the rest of the lines and to the non-transgenic control (p<0.0001).

Example 4. Evaluation of the Tolerance to the Herbicide Glyphosate in the Transgenic Soybean Lines The response of the transgenic plants to glyphosate was evaluated under greenhouse conditions and in field. The application of the herbicide glyphosate under greenhouse conditions was carried out in transformed plants, at 15 days of its adaptation. The herbicide was used to a final dose of 3.5 L/ha, and it was applied by means of a manual sprayer with capacity of 25 L. Two or three days after the application, all the plants sensitive to the herbicide showed chlorosis symptoms, and at 7 days they died. However, the tolerant plants maintained their green coloration. The behavior of the transformed plants in front of the herbicide was similar in both soybean genotypes. All plants of the untransformed control were sensitive to the herbicide. The transgenic plants resistant to the herbicide had a growth and development similar to the untransformed control that was not subjected to the application of the herbicide. The data of the percentage of tolerance to the herbicide in the three evaluated generations (T1, T2 and T3), they are shown in Table 2.

TABLE 2

Evaluation of the tolerance to the herbicide glyphosate in transgenic soybean events and in Dt84 and Is36 untransformed controls under greenhouse conditions.

| | T1 | | T2 | | T3 | |
|---|---|---|---|---|---|---|
| Lines | No. of plants | Resistance to the herbicide (%) | No. of plants | Resistance to the herbicide (%) | No. of plants | Resistance to the herbicide (%) |
| DtDEF1 | 31 | 80.6 | 77 | 100 | 254 | 100 |
| Dt3 | 12 | 83.3 | 73 | 98.6 | 264 | 98.7 |
| Dt4 | 21 | 61.9 | 79 | 98.9 | 91 | 100 |
| Dt5 | 12 | 75 | 72 | 100 | 78 | 100 |
| Dt6 | 13 | 46.1 | 87 | 95.3 | 76 | 98.8 |
| Dt7 | 23 | 61 | 73 | 93.2 | 102 | 98 |
| Dt10 | 13 | 77 | 98 | 92.3 | NE | NE |
| Dt12 | 11 | 91 | 201 | 92 | 209 | 100 |
| Dt14 | 24 | 66 | 104 | 83.7 | NE | NE |
| Dt84 | 15 | 0 | 200 | 0 | 300 | 0 |
| Is1 | 12 | 75 | 136 | 86 | 212 | 100 |
| Is3 | 15 | 73 | 144 | 80 | 229 | 100 |
| Is4 | 14 | 86 | 181 | 87.8 | 406 | 96.0 |
| IsDef5 | 10 | 76 | 177 | 84.2 | 350 | 100 |
| Is19 | 10 | 40 | NE | NE | NE | NE |
| Is20 | 8 | 37 | NE | NE | NE | NE |
| Is36 | 12 | 0 | 201 | 0 | 276 | 0 |

NE: not evaluated

The evaluation of the tolerance to the herbicide under greenhouse conditions showed a group of transgenic lines that presented 80% or more than the plants tolerant to the herbicide in the T1 generation. On the contrary, lines Is19 and Is20 were those with a larger number of plants sensitive to glyphosate, so were not evaluated in the following generations. Starting from the T2 generation, for DtDef1 and Dt5 100% of tolerance to the herbicide was observed, achieving homozygosis with relation to the cp4epsps gene. The rest of the evaluated events showed tolerance to the herbicide in the T3 generation, and in line IsDef5 100% of plants resistant to the herbicide were achieved in the T3 generation.

Example 5. Evaluation of the Infection by Fusarium in Transgenic Soybean Lines

For the test, young and healthy leaves of transgenic plants of the T0 generation were used, grown in greenhouse, of the genotype Dt84 derived lines. The fungus was cultured in Potato-Dextrose-Agar, to a temperature of 28° C., during 7 days. The leaves were placed with the back side facing up, in Petri dishes with 1 mL of sterile distilled water. Later on, a disk was placed (of 5 mm diameter) of medium Potato-Dextrose-Agar with *Fusarium* sp. fungus in the center of the leaf. The leaves were incubated at 28° C., to be observed at 7, 10, 15 and 25 days after inoculation. They put two controls of untransformed plants: a positive control (leaves with disks of the fungus) and a negative control (leaves without disks of the fungus). The infection index was calculated, measuring the area of the leaf affected by the disease caused by the presence of the fungus, by means of the 4-degree scale of proposed by Ntui and collaborators (Ntui et al., Plant Cell Report (2010) 29:943-54). In the leaves of the untransformed control the first symptoms appeared around the fungus, in chlorosis form, at 7 days after the inoculation, and it was observed that the mycelium of the fungus grew on these leaves. At 10 days, the leaves showed necrosis in the center of the chlorotic halo, embracing around 50% of the foliar area. That necrosis embraced 75% of the leaf, after 15 days. At 25 days, 100% of the leaves were necrotic, and they turned translucent in the control. On the contrary, in the leaves of plants transformed genetically these symptoms were not observed with that so advanced level of affectation. The Dt3 and Dt4 events showed a nerval chlorosis in the leaves, 10 days after the inoculation and a slight necrosis in the central nerve. These lesions embraced less than 12% of the total area of the leaf in both lines. On the other hand, in the DtDef1 line there wasn't an affectation by *Fusarium* sp. fungus, and all the leaves maintained their intense green coloration. The infection index observed in some of the lines evaluated in this experiment is shown in Table 3.

TABLE 3

Infection index in leaves of transgenic soybean plants and untransformed control inoculated with *Fusarium* sp.

| Transgenic lines (T0) | Infection Index | Assessment against the fungus |
|---|---|---|
| DtDef1 | 0.025 | Resistant |
| Dt3 | 0.025 | Resistant |
| Dt4 | 0.025 | Resistant |
| Dt84 | 33.1 | Highly susceptible |

Keeping in mind the results obtained in the bioassays with T0 generation, the three evaluated lines were classified as resistant, due to their low index of infection (0.025-1.20). On the other hand, the untransformed control was classified as highly susceptible, for its high infection index (33.1), as it is shown in Table 3.

Example 6. Response of the Transgenic Lines Against Natural Infection by *Phakopsora pachyrhizi* Under Conditions of Culture House This experiment was carried out with the T1 generation of transgenic lines DtDef1, Dt3, Dt4, Dt5, Dt6, and a non-transgenic control (Dt84). The plants, planted in stonemasons of the mesh house, were not exposed to any application of chemical products. The presence of Asian rust in areas near to the mesh house makes that uredospores that are produced in the sick plants, be dragged by currents of air, and be dispersed at big distances. For it, the plants were observed every 3 days, to evaluate them as for the incidence of *P. pachyrhizi* fungus. Similar symptoms to those described in the literature, for Asian rust, were observed in all the plants of the non-transgenic control planted in the mesh house. Some leaves of the control presented pocks of brown-reddish color, in the back of the leaves of the inferior third of the plant, chlorosis that ended up covering the whole leaf, and some plants showed defoliation, being the petiole stuck to the stem. Some of those symptoms were also observed in leaves of the transgenic lines, as chlorosis and pocks in the back of the leaves in the basal area near to the floor, but these did not affect the superior third of the plants.

The presence of the Asian rust disease was confirmed with the strips of the Envirologix QuickStix® immunodetection kit, for the detection of *P. pachyrhizi*. This test was positive in the plants of the untransformed control and of the transformed lines; although in the transgenic plants few symptoms were observed in the leaves. For the immunodetection, a portion of the sample of 2.5 cm of diameter is taken and is placed in a mesh bag. The sample is rubbed through the surface of the mesh bag, and 5 mL of extraction buffer is added. Finally, 200 µL of the solution are transferred to an Eppendorf tube and is placed a strip of the kit inside, during 10 minutes. The presence of a second signal, in the inferior part of the strip, indicates the presence of Asian rust in the analyzed sample. This test allows detecting the presence of the pathogen in very early stages of the infection. As a confirmation, the samples of the tissue of leaves with the presence of Asian rust were taken to the stereoscope and the optic microscope, and pocks (uredias) of brown color, typical of Asian rust were visualized, so much in the plants of the control as in the plants of the transgenic lines affected.

Figure 8:
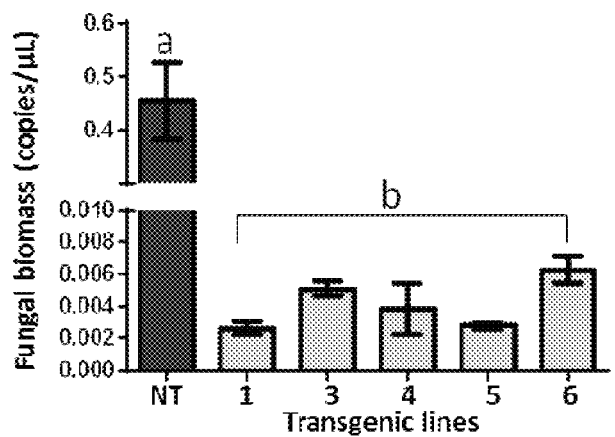
FIG. 8. Quantification of the biomass of the fungus *P. pachyrhizi* present in the transgenic soybean lines DtDef1, Dt3, Dt4, Dt5 and Dt6, and in the Dt84 untransformed control. Quantification was made by qRT-PCR.
Figure 9:
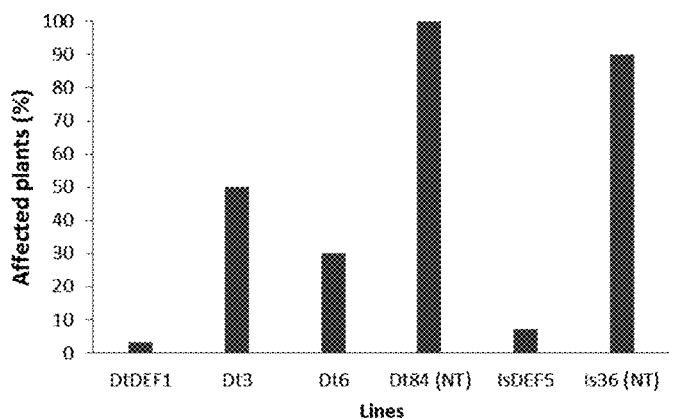
FIG. 9. Incidence of Asian rust in soybean plants sowed in an experimental parcel, expressed as percentage of affected plants. Transgenic lines: DtDef1, Dt3, Dt6 and IsDef5. Untransformed controls: Dt84 (NT) and Is36 (NT).
Figure 10:
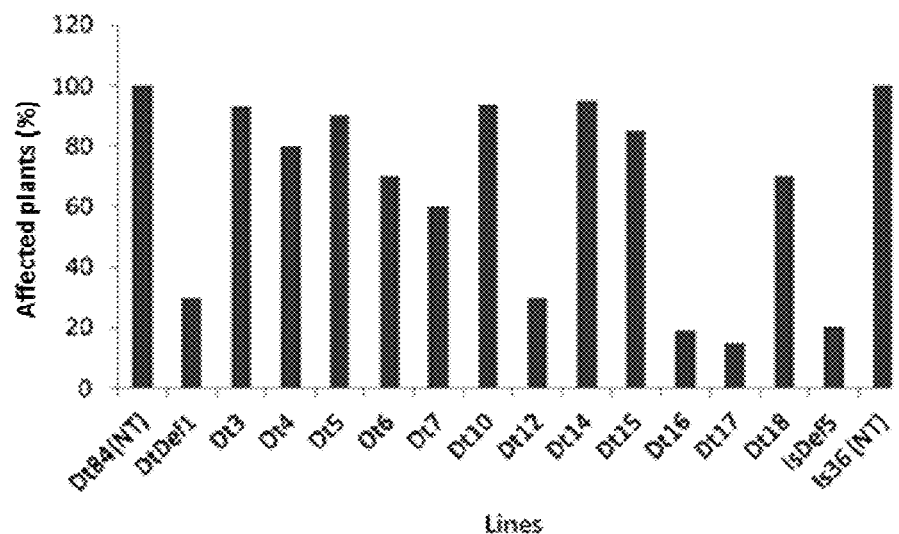
FIG. 10. Incidence of Asian rust in transgenic soybean plants and in the untransformed controls Dt84 (NT) and Is36 (NT). The percentage of plants affected by the fungus *P. pachyrhizi* in several transgenic lines is shown.

Later on, the DNA of the transformed plants was analyzed and the control Dt84, affected or not by the *P. pachyrhizi* fungus, by means of qRT-PCR, with the specific oligonucleotides of the Asian rust (Sconyers, et al., Plant Disease (2006) 90:972-972). This way the biomass of the fungus present in the affected plants was quantified, and the obtained data are shown in FIG. 8. The quantification of the biomass of the fungus, present in the plants, demonstrated that there was a significant difference between control and the transformed lines, since the latter ones showed very inferior levels of presence of the fungus. This confirms the resistance observed in the leaves of the transformed plants, in front of the biotrophic fungus causing the Asian rust, mainly in DtDef1 and Dt5.

The evaluated lines were harvested, and there was made an agronomic evaluation, where there were considered different parameters related to the yield. In the agronomic evaluation it was confirmed that the transgenic plants did not show affectations in any of their organs, and their phenotypical characteristics are similar to those of the control. The evaluated parameters were similar among the five transgenic lines, except for the number and weight of the seeds that was larger in the DtDef1, Dt4 and Dt5 lines. There was a reduction in the yields of the control Dt84, when it was compared with three of the transgenic lines, just as it is appreciated in Table 4.

TABLE 4

Morpho-agronomic evaluation of the transgenic and non-transgenic plants harvested under conditions of culture house.

| Lines | Size (cm) | Height of the first sheath (cm) | Yield (g/plant) | Weight 100 seeds (g) |
|---|---|---|---|---|
| DtDEF1 | 42.28$^a$ | 7.21$^a$ | 29.53$^a$ | 20.55$^a$ |
| Dt4 | 32.60$^b$ | 6.65$^{ab}$ | 11.60$^c$ | 16.97$^c$ |
| Dt5 | 26.71$^c$ | 6.79$^{ab}$ | 14.00$^b$ | 18.42$^{bc}$ |
| Dt84 | 28.44$^c$ | 6.04$^b$ | 10.25$^b$ | 18.77$^b$ |

Means with different letters in a same column of the table indicate significant statistical differences for p<0.05, according to the Tukey test. The data correspond to the mean of 30 plants for each line.

Figure 11:
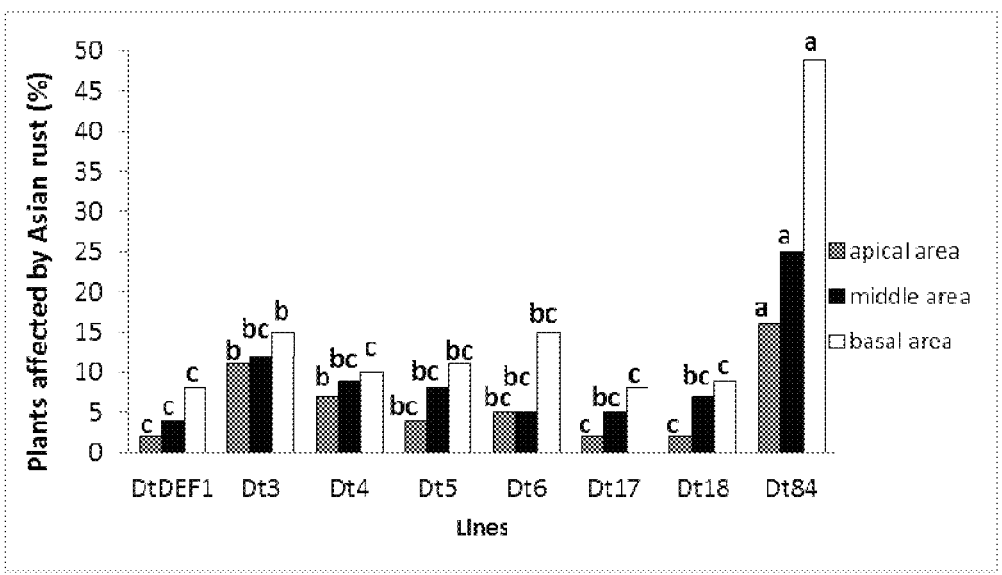
FIG. 11. Evaluation of the severity of Asian rust in transgenic soybean plants that express the nmdef02 and cp4epsps genes, and in the untransformed control (Dt84), sowed in the field.

Example 7. Response of the Transgenic Lines Against the Natural Infection by *Phakopsora pachyrhizi* on Field Conditions The evaluation of the incidence of *P. pachyrhizi* in transgenic soybean lines that express the defensin gene and the gene responsible for the tolerance to glyphosate was carried out during the months of November-February, when the climatic conditions favor the development of fungal diseases. Transgenic lines DtDef1, Dt3 and Dt6, and the untransformed control were evaluated (Dt84), as well as the IsDef5 line with their respective control (Is36). The first symptoms of affectation by Asian rust were observed in the non-transgenic control, when the plants were in the phase of filling the grain. The presence of the disease was confirmed with the Envirologix QuickStix® immunodetection kit for the detection of Asian rust. This test was positive for the control, with a high degree of affectation in the leaves, and for the transformed lines, in spite of being observed very few symptoms in the leaves. However, the transgenic lines that had up to 50% of presence of symptoms of Asian rust presented a sensitive recovery of their phenotype and of yield in the production of grains per plant. Therefore, it was considered that the lines were resistant to fungi, in particular to the Asian rust, when the plants did not overcome 50% of presence of symptoms of this disease.

In the field evaluation it was observed that the Dt3 and Dt6 lines were affected by rust, but the affectation was inferior to the one observed in the Dt84 non-transgenic control, as it is shown in FIG. 9. On the other hand, clone DtDef1 showed a low incidence of the fungus, and only small necrotic points were observed in leaves of the basal part of some plants, contrary to control Dt84 that had 100% of affectation by Asian rust. In that control group a general chlorosis was observed, pocks in the leaves and precocious defoliation in all the plants. In turn, the IsDef5 line showed a low affectation for rust in the plants, of less than 5%, compared with more than 80% of plants affected in genotype Is36, used as untransformed control of the experiment. At the end of the cycle the plants were harvested and different parameters related with yield were evaluated. These were superior, with statistical significance, in the DtDef1 line regarding the untransformed control and the rest of the transgenic lines evaluated in this experiment.

In a second experiment, it was carried out the evaluation of the transgenic lines (genotype Dt84) in front of the infection by Asian rust of soybean, in an experimental plot, during the months of November-February, coinciding with the most favorable time for the development of the infection. The first rust symptoms appeared very early, when the plants were in the budding and formation of the grain phase. These were observed in the untransformed controls and in some transgenic lines. The presence of the disease was confirmed by the Envirologix QuickStix® immunodetection kit, being positive for the control and the transformed lines.

In the same experiment, also, the incidence of the disease as the percent of affected plants was quantified, where the transgenic lines had some degree of affectation by Asian rust. These plants showed values of incidence lower than those of the untransformed control, as it is appreciated in FIG. 10. The DtDef1, Dt12, Dt16, Dt17 and IsDef5 lines were those of lesser percent of incidence.

The severity of the disease (percentage of the area of the leaf affected by rust) was analyzed using the scale proposed in 2006, by Ploper and collaborators (Ploper et al., Avance agroindustrial-Estación Experimental Agro-Industrial Obispo Colombres (2006) 27: 35-37). For this there were sampled leaflets of the basal, medium and apical areas of the plants. The results that are shown in FIG. 11 indicate that the values of severity, expressed in percent of affectation, were larger in the basal area than in the medium area, and these in turn were larger than those of the apical area. All the transgenic lines showed smaller severity of the disease that control Dt84, which had more than 40% affectation by rust in the leaves of the basal area. The plants of the DtDef1, Dt17 and Dt18 lines showed lesser affectation by Asian rust; of them the DtDef1 line had less than 8% of leaves affected in the basal area, with inferior values to 5% in the medium and apical areas.

In this same test, the plants used as negative controls (genotype Dt84) had 100% of incidence of this disease, which demonstrates the high susceptibility of this genotype to the Asian rust. The transgenic plants of the evaluated susceptible lines had a rust incidence that oscillated between 58-97%. However, the plants of the resistant transgenic lines had an incidence of 16-35%. In the evaluations it was verified that the leaves of the transgenic plants maintained their green coloration, in spite of the incidence of the pathogen, contrary to the non-transgenic control that showed chlorosis in its leaves, followed by a widespread defoliation.

Figure 12:
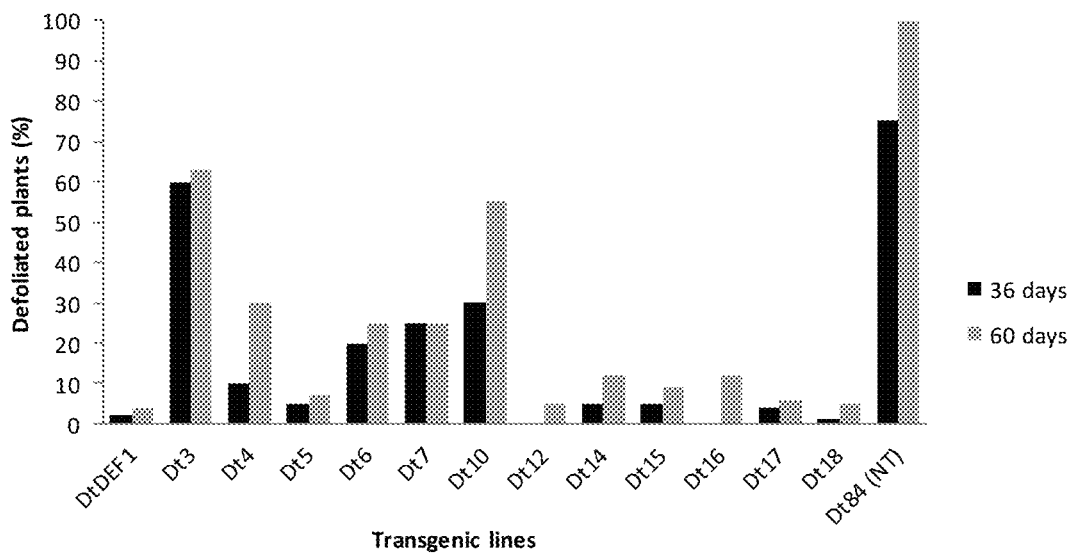
FIG. 12. Defoliation percentage (plant without leaves) due to the incidence of Asian rust in the transgenic lines and in the Dt84 untransformed control (NT), 36 and 60 days after the detection of the disease.

Another evaluated parameter was the defoliation of the plants affected by *P. pachyrhizi*, 36 and 60 days after the symptoms of the disease were detected (FIG. 12). The results show that the transformed plants had a percentage of defoliation inferior to those of the untransformed control Dt84. In this evaluation it was observed that, at 36 days, the Dt12 and Dt16 lines did not defoliate. In this same time, lines Dt1, Dt5, Dt17 and Dt18 had a defoliation percentage smaller than 10%. Also, at 60 days of the evaluation of these lines, the defoliation values did not exceed 10%. The DtDef1 line showed resistance to this pathogen, and the defoliation was smaller than 5%.

Figure 13:
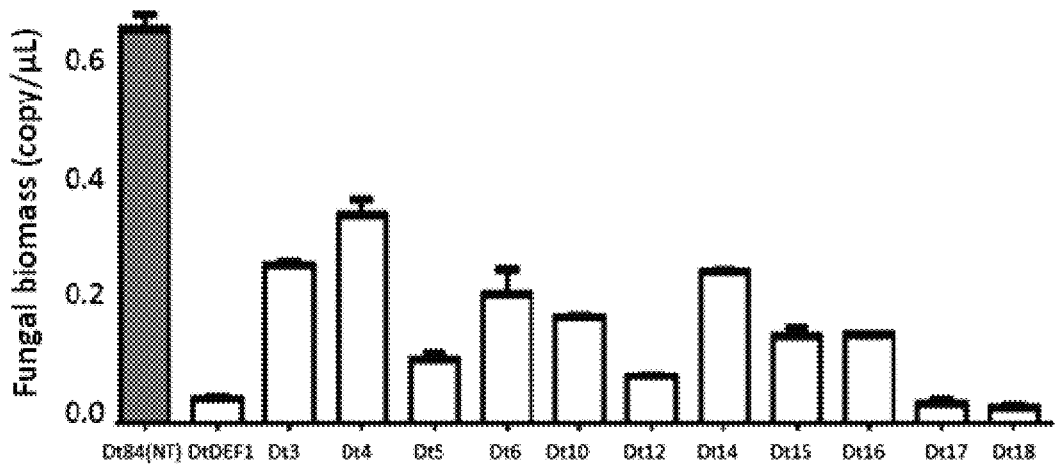
FIG. 13. Quantification of the biomass of *P. pachyrhizi* in soybean plants of different transgenic lines and of the Dt84 untransformed control (NT). The quantification was carried out by qRT-PCR.

In that same experiment it was also carried out the quantification of the biomass of the *P. pachyrhizi* fungus present in the affected plants. This analysis was made by means of qRT-PCR, with specific oligonucleotides for the fungus, that which allowed to confirm the species of the pathogen. All the transgenic lines had a smaller quantity of biomass of the pathogen, in comparison with the untransformed control. The lines DtDef1, Dt17 and Dt18 showed a smaller biomass of the fungus present in the plants (FIG. 13), and they had a significant difference with the non-transgenic control ($p<0.0001$). These results demonstrate the antifungal effect of the nmdef02 defensin expressed in the soybean in front of Asian rust, on field conditions.

In the analysis of the leaves affected by *P. pachyrhizi* fungus an abundant sporulation was observed in the pocks (or uredia) of the non-transgenic plants, which coincides with the high number of copies of the fungus in these control plants. In the transgenic plants, the uredospores production was much reduced in some lines (DtDef1, Dt12, Dt17 and Dt18), coinciding with the lesser quantity in fungus biomass. In some plants of these lines, although there were formed uredia, there was no spore production, which demonstrates that there is a resistance response to *P. pachyrhizi*.

At the end of the cycle, the plants were harvested, and different parameters related with the yield were evaluated. In Table 5 some results of the evaluation of the crop of the plants are shown, there was a high difference between the transgenic lines and the control. Defoliation, superior to 20% in the near stages to grain filling (R3 to R5), caused an affectation of the yields in the untransformed controls.

TABLE 5

Morpho-agronomic evaluation of the transgenic and non-transgenic plants harvested under conditions of experimental parcel.

| Lines | Size (cm) | Height first sheath (cm) | Yield (g/plant) |
|---|---|---|---|
| DTDef1 | $35.8^{bc}$ | $8.4^{ab}$ | $11.5^{ab}$ |
| Dt4 | $34.3^{cd}$ | $7.0^{bcd}$ | $10.3^{abc}$ |
| Dt10 | $31.8^{cde}$ | $6.2^{d}$ | $8.6^{bcde}$ |
| Dt12 | $40.9^{ab}$ | $7.8^{abc}$ | $8.1^{bcde}$ |
| Dt14 | $32.2^{cde}$ | $6.3^{cd}$ | $8.3^{bcde}$ |
| Dt15 | $27.4^{efg}$ | $6.7^{cd}$ | $7.6^{cdef}$ |
| Dt16 | $42.8^{a}$ | $9.3^{a}$ | $10.8^{ab}$ |
| Dt17 | $34.5^{cd}$ | $7.5^{abc}$ | $9.0^{abcd}$ |
| Dt18 | $35.1^{dc}$ | $7.7^{bcd}$ | $11.0^{ab}$ |
| Dt84 | $27.6^{efg}$ | $6.6^{cd}$ | $4.7^{f}$ |
| IsDef5 | $40.8^{ab}$ | $7.7^{bcd}$ | $11.7^{a}$ |
| Is36 | $35.0^{cd}$ | $8.0^{bcd}$ | $8.5^{bcde}$ |

Means (of 30 plants for line) with different letters in a same column indicate significant statistical differences for $p<0.05$, according to the test of Tukey.

Most of the transgenic lines had statistically significant differences with the genetically untransformed control. The affectation by the pathogen, in an early development stage of the crop, impacted in the low yields observed in the control. This affectation by the pathogen diminished the number of branches, sheaths and seeds, as well as the weight of the seeds per plant.

On the base of the obtained response, as for the severity of the symptoms produced by *P. pachyrhizi*, the percentage of defoliation of the soybean plants, and the yield of the transgenic lines evaluated in field it was determined that the CIGBDt-Def1 and CIGBIs-Def5 transgenic events had the best behavior for their use in soybean crop with commercial interest.

Example 8. Identification of the Site of Insertion of the Transgene in the Genome of the CIGBDtDef1 Event The extraction of total DNA of the transgenic line was carried out, by means of the CTAB protocol reported by Doyle and Doyle (1987) modified, which was followed by its massive sequence by means of Illumina HiSeq 2500, by the Macrogen Company (South Korea). The sequences were checked by the FastQC program (version 0.11.4), and it was proven that they follow the expected quality pattern for the used platform (Illumina HiSeq 2500). For mapping the sequenced readings to the genome of soybean and the vector, and identifying the possible sites of insert of the transgene, program ITIS was used (version 1). ITIS is a program designed for transposon identification starting from data of massive sequencing in parallel (SMP), which is a similar application to the one of identifying a vector in a genome. ITIS makes use of the characteristics of the paired extreme technology of Ilumina Platform. In it, each fragment of the bookstore is object of 2 readings. One from extreme 5' to extreme 3' and the other one in the opposite direction, from extreme 3' to extreme 5'. Both readings are considered a pair. ITIS makes use of the bwa program (version 0.7.7) to align the readings to the genome and the vector. The analysis of the mapped sequences to the vector indicated that a large part of them has little covering, except for those that are located in chromosome 2. For that reason, it was decided to continue the analysis in the readings mapped in this chromosome and in the vector (that is represented in FIG. 1). As a result, two potential sites of insert of the transgene were identified in chromosome 2 of the soybean genome (DtDef1 line), in positions 8002360 and 8334726. These positions refer to the numbers of the nucleotides in the genome of the Willian82 soybean variety.

Figure 14:
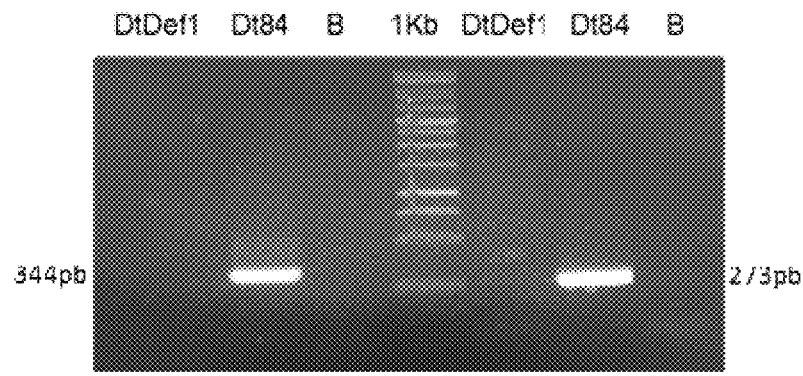
FIG. 14. PCR products from DNA of soybean plants (DtDef1 Line) and of the non-transgenic control, with primers designed in regions of the soybean genome adjacent to the sites identified in the bioinformatic analysis. Amplification of a 344 bp sequence corresponding to the 8002360 site and a sequence of 273 bp corresponding to the 8334726 site in the untransformed soybean plant. Lanes: 1 Kb: Molecular weight marker (Promega), DTDef1: DTDef1 transgenic soybean line. Dt84: untransformed soybean plant. B: blank.

The insert of the transgene in sites 8002360 and 8334726 was validated by means of PCR, with primers designed in the regions of the soybean genome adjacent with the sites identified in the biocomputer analysis. For site 8002360, the sequences of the primers were: 3'-AAGCGGCAAGT-CAATCGTGTCG-5' (SEQ ID NO: 1) and 5"-CT-GAATCCCTACATTGCGATTCTCG-3' (SEQ ID NO: 2) whose combination generated a band to the size of 344 bp with the soybean DNA without genetic modification, as it is shown in FIG. 14. For site 8334726, the sequences of the primers were: 3'-ATGTGCAATAATTCCTTCTTCG-5' (SEQ ID NO: 3) and 5'-CGAAACACGAATCACGAAGC-3' (SEQ ID NO: 4), this combination generated a band to the size of 273 bp with the soybean DNA without genetic modification (FIG. 14). In the transgenic line no band was amplified, when carrying out the procedure with both oligonucleotide pairs. The results obtained confirm the insert of the transgene in sites 8002360 and 8334726, both in the chromosome 2 of the soybean.

Figure 15:
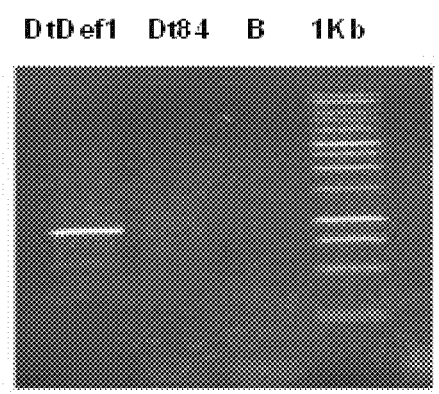
FIG. 15. PCR products from DNA of plants of the CIGBDtDef1 transgenic line and of the non-transgenic control, obtained with the combination of soybean primers with primers of the cp4epsps gene in the pCP4EPSPS-Def vector (FIG. 1). Amplification of a 1000 bp sequence in the site 8002360 (A) and 900 bp in the site 8334726 (B), for the CIGBDtDef1 transgenic event. Lanes: 1 Kb: Molecular weight marker (Promega). DTDef1: Soybean transgenic line. Dt84: untransformed soybean plant. B: Blank.
Figure 15:
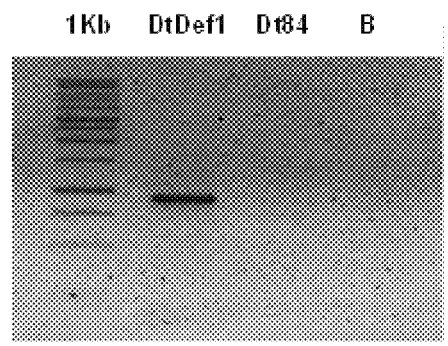

Later on, the primers designed from the sequence of the soybean genome were combined with primers in genes cp4epsps and nmdef02, both in the pCP4EPSPS-Def vector (which is represented in FIG. 1). The combination of primers (Forward and Reverse) in the soybean with primers in the cp4epsps gene (5'-GGATTTCAGCATCAGTGGCTA-CAGC-3') (SEQ ID NO: 5) and (3'-GCGGGTT-GATGACTTCGATGTCG-5') (SEQ ID NO: 6) confirmed the presence of the transgene in sites 8002360 (FIG. 15A) and 8334726 (FIG. 15B), for the CIGBDtDef1 transgenic event. In FIG. 15A the amplification of a sequence of 1000 bp is observed in site 8002360, and in FIG. 16B the amplification of a sequence of 900 bp is observed in site 8334726, for the CIGBDtDef1 transgenic event. These amplified regions correspond to nucleotide sequences that contain so much nucleotides of the plant, as of the introduced transgene.

Figure 16:
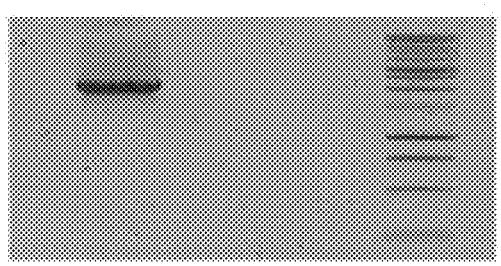
FIG. 16. PCR products from DNA of the CIGBDtDef1 transgenic line and of the non-transgenic control, obtained with the combination of soybean primers and primers of the nmdef02 gene in the pCP4EPSPS-Def vector (FIG. 1). Amplification of a 2000 bp sequence in the 8002360 site (A) and 300 bp in the 8334726 site (B), for the CIGBDtDef1 transgenic event. Lanes: 1 Kb: Molecular weight marker (Promega). DTDef1: Soybean transgenic line. Dt84: untransformed soybean plant. B: Blank.
Figure 16:
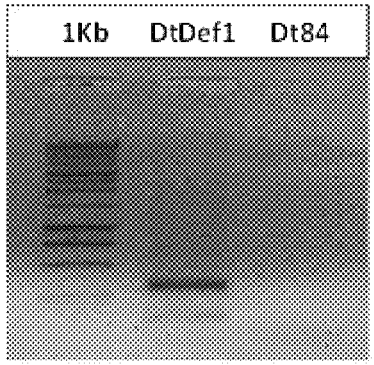

The same thing happened when using the combination of primers designed from the sequence of the soybean genome with primers designed for the nmdef02 gene (3'-GCTGGCTTATGCTTCCTCTTCTTG-5') (SEQ ID NO: 7) (5'-TCACAGACTTGGACGCAGTTCG-3') (SEQ ID NO: 8), for sites 8002360 (FIG. 16A) and 8334726 (FIG. 16B). In FIG. 16A the amplification of a sequence of 2000 bp is observed in site 8002360, and in FIG. 16B the amplification of a sequence of 300 bp is observed in site 8334726, for the CIGBDtDef1 transgenic event. These amplified regions correspond to nucleotide sequences that contain so much nucleotides of the plant as of the introduced transgene. In this way, the insertion of the transgene into the event DtDef1 is demonstrated.

INCORPORATION OF SEQUENCE LISTING

Incorporated herein by reference in its entirety is the Sequence Listing for the application. The Sequence Listing is disclosed on a computer-readable ASCII text file titled, "Sequence_Listing_976-105PCTUS.txt", created on Apr. 14, 2021. The sequence_listing.txt file is 1.5 KB in size.

The invention claimed is:

1. A soybean plant or a part of said plant comprising the transgenic event CIGBDt-Def1 or the transgenic event CIGBIs-Def5, where soybean seeds representative of said events were deposited in the National Collection of Industrial, Food and Marine Bacteria (NCIMB) of the United Kingdom under access number NCIMB 42724 for CIGBDt-Def1 event and NCIMB 42725 for CIGBIs-Def5 event.

2. A progeny soybean plant of any generation of the soybean plant of claim 1, wherein the progeny plant comprises the soybean event CIGBDt-Def1 or the soybean event CIGBIs-Def5.

3. A soybean plant produced from crossing the soybean plant of claim 1 with another soybean plant lacking the event, wherein the soybean plant resulting from the cross comprises the soybean event CIGBDt-Def1 or the soybean event CIGBIs-Def5.

4. The soybean plant or part of said plant of claim 1, wherein the part is a root, bud, leaf, pollen, ovum, flower or cell.

5. A seed of a soybean plant comprising the event CIGBDt-Def1 or the event CIGBIs-Def5, where soybean seeds representative of said events were deposited in the National Collection of Industrial, Food and Marine Bacteria (NCIMB) of the United Kingdom under access number NCIMB 42724 for CIGBDt-Def1 event and NCIMB 42725 for CIGBIs-Def5 event, wherein the seed comprises the event CIGBDt-Def1 or the event CIGBIs-Def5.

6. A soybean product produced from a plant or from a soybean seed comprising the event CIGBDt-Def1 or the event CIGBIs-Def5, where soybean seeds representative of said events were deposited in the National Collection of Industrial, Food and Marine Bacteria (NCIMB) of the United Kingdom under access number NCIMB 42724 for CIGBDt-Def1 event and NCIMB 42725 for CIGBIs-Def5 event, wherein the product comprises the event CIGBDt-Def1 or the event CIGBIs-Def5.

7. The product of claim 6 that is flour, flakes, oil or a product for human or animal feeding.

8. A method for the production of a soybean plant resistant to the herbicide glyphosate and to diseases caused by fungi or oomycetes, the method comprising introducing the event CIGBDt-Def1 or the event CIGBIs-Def5 into the genome of said plant, where soybean seeds representative of said events were deposited in the National Collection of Industrial, Food and Marine Bacteria (NCIMB) of the United Kingdom under access number NCIMB 42724 for CIGBDt-Def1 event and NCIMB 42725 for CIGBIs-Def5 event.

9. The method of claim 8 wherein the soybean disease is the Asian rust caused by *Phakopsora pachyrhizi*.

10. The method of claim 8 comprising crossing a soybean plant comprising the event CIGBDt-Def1 or the event CIGBIs-Def5 with another soybean plant, and selecting a progeny comprising the event CIGBDt-Def1 or the event CIGBIs-Def5.

11. A method for the diagnosis of the event CIGBDt-Def1 or the event CIGBIs-Def5 in a soybean sample, the method comprising analyzing said sample to detect the presence of nucleic acid or protein corresponding to the event CIGBDt-Def1 or the event CIGBIs-Def5 by using an oligonucleotide pair for the amplification of fragments of nucleic acid corresponding to the union regions between the nucleic acid of a soybean plant and the nucleic acid corresponding to the event CIGBDt-Def1 or to the event CIGBIs-Def5, wherein the oligonucleotide pair is at least one of SEQ ID NO: 1 and SEQ ID NO: 2, or SEQ ID NO: 3 and SEQ ID NO: 4, or SEQ ID NO: 5 and SEQ ID NO: 6, or SEQ ID NO: 7 and SEQ ID NO: 8, where soybean seeds representative of said events were deposited in the National Collection of Industrial, Food and Marine Bacteria (NCIMB) of the United Kingdom under access number NCIMB 42724 for CIGBDt-Def1 event and NCIMB 42725 for CIGBIs-Def5 event.

12. A method to increase the yield of a soybean crop in field comprising:
  a) sowing seeds of a soybean plant comprising the event CIGBDt-Def1 or the event CIGBIs-Def5,
  b) establishing the soybean crop in the field,
  c) treating the field with an effective quantity of the herbicide glyphosate to control weeds, where soybean seeds representative of said events were deposited in the National Collection of Industrial, Food and Marine Bacteria (NCIMB) of the United Kingdom under access number NCIMB 42724 for CIGBDt-Def1 event and NCIMB 42725 for CIGBIs-Def5 event.

13. The method of claim 12 wherein the field is treated between the phases of the crop V1 and R4.

\* \* \* \* \*